United States Patent
Fromm et al.

(10) Patent No.: US 7,380,747 B2
(45) Date of Patent: Jun. 3, 2008

(54) THROUGH-ROLL PROFILE UNWIND CONTROL SYSTEM AND METHOD

(75) Inventors: Gregory Fromm, Neenah, WI (US); Paul Christoffel, Appleton, WI (US)

(73) Assignee: Kimberly-Clark Wolrdwide, Inc., Neenah, WI (US)

( * ) Notice: Subject to any disclaimer, the term of this patent is extended or adjusted under 35 U.S.C. 154(b) by 371 days.

(21) Appl. No.: 11/303,073

(22) Filed: Dec. 14, 2005

(65) Prior Publication Data

US 2007/0131817 A1 Jun. 14, 2007

(51) Int. Cl.
*B65H 43/00* (2006.01)

(52) U.S. Cl. .................................... 242/563.2

(58) Field of Classification Search ............... 242/563, 242/563.2, 564, 564.3, 564.4, 420, 421.2, 242/421.4
See application file for complete search history.

(56) References Cited

U.S. PATENT DOCUMENTS

| | | | |
|---|---|---|---|
| 3,630,463 A | 12/1971 | Mistele |
| 3,692,618 A | 9/1972 | Dorschner et al. |
| 3,849,241 A | 11/1974 | Butin et al. |
| 3,862,724 A | 1/1975 | Johnson et al. |
| 3,889,895 A | 6/1975 | Edes et al. |
| 4,340,563 A | 7/1982 | Appel et al. |
| 4,655,760 A | 4/1987 | Morman et al. |
| 4,657,802 A | 4/1987 | Morman |
| 4,720,415 A | 1/1988 | Wielen et al. |
| 4,729,519 A | 3/1988 | Tafel et al. |
| 4,781,966 A | 11/1988 | Taylor |
| 4,789,699 A | 12/1988 | Kieffer et al. |
| 4,965,122 A | 10/1990 | Morman |
| 4,981,747 A | 1/1991 | Morman |
| 5,114,781 A | 5/1992 | Morman |
| 5,116,662 A | 5/1992 | Morman |
| 5,226,992 A | 7/1993 | Morman |

(Continued)

FOREIGN PATENT DOCUMENTS

EP 0107959 A2 5/1984

(Continued)

OTHER PUBLICATIONS

English language abstract for JP 61-099,507 issued May 17, 1986 to Matsumiya et al.

(Continued)

*Primary Examiner*—Peter M. Cuomo
*Assistant Examiner*—William E Dondero
(74) *Attorney, Agent, or Firm*—Dority & Manning, P.A.

(57) ABSTRACT

A method of unwinding material in a process system for producing a product includes the steps of loading a roll of material in an unwind system, programming a controller with an unwind equation, the controller in communication with the unwind system, computing a material feed rate based on a predetermined product circumference and an average stretch-to-stop roll profile, and putting a diameter of the roll of material and the material feed rate in the unwind equation of the controller, and unwinding a varying amount of material from the roll of material at a varying unwind speed, the controller being responsive to the unwind equation to vary the unwind speed for forming a plurality of products, each product defining a respective circumference substantially equal to the predetermined product circumference.

25 Claims, 6 Drawing Sheets

U.S. PATENT DOCUMENTS

| | | | |
|---|---|---|---|
| 5,336,545 | A | 8/1994 | Morman |
| 5,623,189 | A | 4/1997 | Hemmer |
| 6,012,668 | A | 1/2000 | Zurfluh et al. |
| 6,314,333 | B1 | 11/2001 | Rajala et al. |
| 6,719,240 | B2 | 4/2004 | Hanson et al. |
| 6,740,200 | B2 | 5/2004 | Seymour et al. |
| 6,820,837 | B2 | 11/2004 | Long |
| 2003/0231318 | A1 | 12/2003 | Sartain et al. |
| 2005/0167460 | A1 | 8/2005 | Franz et al. |

FOREIGN PATENT DOCUMENTS

| | | |
|---|---|---|
| JP | 61099507 | 5/1986 |
| JP | 2163265 | 6/1990 |
| JP | 4094357 | 3/1992 |
| WO | WO 9813262 A1 | 4/1998 |

OTHER PUBLICATIONS

English language abstract for JP 2-163,265 issued Jun. 22, 1990 to Ihara et al.

English language abstract for JP 4-094,357 issued Mar. 26, 1992 to Matsumoto.

The International Search Report mailed on Jan. 5, 2007.

THROUGH-ROLL PROFILE UNWIND CONTROL SYSTEM AND METHOD

BACKGROUND OF THE INVENTION

In the paper and plastic film industries, a dancer roll is widely used to maintain constant tension on a continuous web of raw material as the raw material unwinds in a conventional unwind system. More specifically, the unwind system typically uses an air-loaded or weight-loaded dancer bar, roll or festoon carriage to actively control the web tension from the top of a roll of raw material to its core. The conventional unwind system also uses a closed loop software program and a position sensor to determine the dancer or festoon carriage position and to adjust unwind spindle speed to maintain consistent position and through-roll web tension levels.

The conventional unwind method works well for materials with consistent machine direction (MD) stretch, tension and thickness. However, some MD elastomeric raw materials used to produce personal care products contain stretch, basis weight and thickness properties that change from the top of the roll to the core. These variable through-roll stretch properties affect material consumption, product size and fit and overall process control. Conventional unwinds will not compensate for variable MD elastomeric properties, which results in an increased raw material consumption, increased machine cull waste, and products that do not conform to target design criteria.

A process system is needed in the industry that compensates for varying MD elastomeric properties in order to reduce elastomeric material consumption, product variability and overall process variability and down time.

BRIEF SUMMARY OF THE DISCLOSURE

The invention is generally directed to a system and method for passively controlling material feed rate and a maximum product circumference (MPC) by using a feed rate equation derived, for instance, from elastomeric roll sampling and testing to control unwind spindle speed. According to some aspects of the invention, a referenced stretch-to-stop (rSTS) profile is established by the roll sampling and testing to produce the feed rate equation. The rSTS profile is consistent from batch-to-batch, roll-to-roll and deckle-to-deckle for elastomeric materials. As described in detail below, by controlling unwind spindle speed according to the feed rate equation, web feed can be controlled such that material consumption is reduced and products are sized consistently.

The component parts of the system described herein are simple and economical to manufacture, assemble and use. Other advantages of the invention will be apparent from the following description and the attached drawings or can be learned through practice of the invention.

According to an aspect of the invention, a method of unwinding material in a process system for producing a product includes the steps of loading a roll of material such as elastomeric material in an unwind system, the roll of material defining a diameter; programming a controller with an unwind equation, the controller in communication with the unwind system; computing a material feed rate based on a predetermined product circumference and an average stretch-to-stop roll profile; inputting the diameter of the roll of material and the material feed rate in the unwind equation of the controller; and unwinding a varying amount of material from the roll of material at a varying unwind speed, the controller being responsive to the unwind equation to vary the unwind speed for forming a plurality of products, each product defining a respective circumference substantially equal to the predetermined product circumference. In this aspect, the controller can be a computer or a programmable logic controller.

Also in this aspect of the invention, the material feed rate is defined as the predetermined product circumference/([(the average roll stretch-to-stop profile/100%)+1]×2). The circumferences include a waist-opening circumference, a hip circumference or a leg-opening circumference. A respective circumference is within a predetermined margin of error of the predetermined product circumference; for example, from about 0.05% to about 5%.

The method in this aspect can further include the step of sampling a plurality of roll diameters of a plurality of rolls to determine the average stretch-to-stop roll profile. The method can include sampling a plurality of roll diameters of a plurality of rolls from batch to batch, deckle to deckle, or lane to lane within a deckle to determine the average stretch-to-stop roll profile. The method can also include the step of loading the controller with a statistical analysis program, the statistical analysis program being configured to implement the unwind equation. Additionally, the step of sensing the diameter of the roll of material with a roll diameter sensor can be included in the method. Yet another step according to this method is the step of sensing the diameter of the roll of material with a laser, electro-optic optic roll diameter sensor, an acoustic sensor, an electromagnetic sensor or combinations of these sensors.

In another aspect of the invention, a method of unwinding material in a process system for producing a product includes the steps of determining an average stretch-to-stop roll profile; loading a roll of elastomeric material in an unwind system; sensing a diameter of the roll of elastomeric material; programming a controller with an unwind equation, the controller in communication with the unwind system; computing a material feed rate based on a predetermined product circumference and the average stretch-to-stop roll profile; inputting the diameter of the roll of elastomeric material and the material feed rate in the unwind equation of the controller; and unwinding a varying amount of elastomeric material from the roll of elastomeric material at a varying unwind speed, the controller being responsive to the unwind equation to vary the unwind speed for forming a plurality of products having substantially similar circumferences. In this aspect, the controller can be a computer or a programmable logic controller.

The material feed rate in this aspect of the invention is defined as the predetermined product circumference/([(the average roll stretch-to-stop profile/100%)+1]×2). The circumferences are one of a waist-opening circumference, a hip circumference or a leg-opening circumference. The circumferences are within a predetermined margin of error of the predetermined product circumference. The predetermined margin of error is from about 0.05% to about 5%.

The method in this aspect of the invention can further include the step of sampling a plurality of roll diameters of a plurality of rolls to determine the average stretch-to-stop roll profile. The step of sampling can be sampling a plurality of rolls from batch to batch, deckle-to-deckle, or lane-to-lane within a deckle to determine the average stretch-to-stop roll profile.

In yet another step according to this method, the controller can be programmed with a statistical analysis program, the statistical analysis program being configured to implement the unwind equation in the controller. A further step is to sense the diameter of the roll of material with a roll diameter sensor. The sensor can be a laser, an electro-optic (e.g., camera) sensor, an electromagnetic sensor or the like and combinations of such sensors.

According to another aspect of the invention, a process system for unwinding material to produce a product includes an open-loop unwind system for unwinding a roll of elastomeric material; a sensor for sensing a diameter of the roll of elastomeric material disposed in the open-loop unwind system; and a controller in communication with the open-loop unwind system and the sensor, the controller being configured for programming with an unwind equation for compensating through-roll variability, the unwind equation being populated with the diameter of the roll of elastomeric material and a material feed rate as a function of a predetermined product circumference and an average stretch-to-stop roll profile, the unwind equation of the controller being configured to vary an unwind speed of the open-loop unwind system such that a varying amount of material from the roll of material is unwound for forming a plurality of products, each product defining a respective circumference substantially equal to the predetermined product circumference. The controller can be a computer or a programmable logic controller, and can further include a statistical analysis program to implement the unwind equation in the controller. Also in this aspect, the sensor can be a laser, an electro-optic (e.g., camera) sensor, an electromagnetic sensor or the like and combinations of such sensors in communication with the controller.

In this aspect of the invention, the material feed rate is defined as the predetermined product circumference/([(the average roll stretch-to-stop profile/100%)+1]×2). Also in this aspect, the respective circumference is one of a waist-opening circumference, a hip circumference or a leg-opening circumference. The respective circumference is within a predetermined margin of error of the predetermined product circumference. The predetermined margin of error is from about 0.05% to about 5%.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Repeat use of reference characters in the present specification and drawings is intended to represent the same or analogous features or elements of the present invention.

DEFINITIONS

Within the context of the present description, the following terms may have the following meanings:

"Machine direction" (MD) refers to the length of a fabric or material in the direction in which it is produced or converted, as opposed to "cross direction" or "cross-machine direction" (CD or CMD), which refers to the width of a fabric in a direction generally perpendicular to the machine direction.

"Attached" and "joined" refers to the bonding, adhering, connecting, and any other method for attaching or joining two elements. Two elements will be considered to be attached or joined together when they are bonded directly to one another or indirectly to one another, such as when each is directly attached to an intermediate element.

"Sheet" refers to a layer, which may be a film, a foram, or a nonwoven web.

"Member" when used in the singular can refer to a single element or a plurality of elements.

The term "composite nonwoven fabric", "composite nonwoven", "laminate", or "nonwoven laminate", as used herein, unless otherwise defined, refers to a material having at least one elastic material joined to at least one sheet material. In most embodiments such laminates or composite fabric will have a gatherable layer, which is bonded to an elastic layer or material so that the gatherable layer may be gathered between bonding locations. As set forth herein, the composite elastic laminate may be stretched to the extent that the gatherable material gathered between the bond locations allows the elastic material to elongate. This type of composite elastic laminate is disclosed, for example, in U.S. Pat. No. 4,720,415 to Vander Wielen et al., which is incorporated herein in its entirety by reference thereto.

As used herein, the term "nonwoven web" refers to a web having a structure of individual fibers or threads that are interlaid, but not in an identifiable, repeating manner. Nonwoven webs have been, in the past, formed by a variety of processes such as, for example, meltblowing processes, spunbonding processes and bonded carded web processes.

The term "continuous filaments", as used herein, refers to strands of continuously formed polymeric filaments. Such filaments will typically be formed by extruding molten material through a die head having a certain type and arrangement of capillary holes therein.

As used herein, the term "meltblown fibers" means fibers formed by extruding a molten thermoplastic material through a plurality of fine, usually circular, die capillaries as molten thermoplastic material or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, U.S. Pat. No. 3,849,241 to Butin, which is incorporated herein in its entirety by reference thereto.

As used herein, the term "spunbonded fibers" refers to small diameter fibers formed by extruding a molten thermoplastic material as filaments from a plurality of fine, usually circular, capillaries of a spinerette with the diameter of the extruded filaments then being rapidly reduced as by, for example, eductive stretching or other well-known spun-bonding mechanisms. The production of spun-bonded non-woven webs is illustrated in patents such as, for example, U.S. Pat. No. 4,340,563 to Appel et al., and U.S. Pat. No. 3,692,618 to Dorschner et al. The disclosures of these patents are incorporated herein in their entireties by reference thereto.

"Extendable" or "extensible" means that property of a material or composite by virtue of which it stretches or extends in the direction of an applied biasing force by at least about 25% of its relaxed length. An extendable material does not necessarily have recovery properties. For example, an elastomeric material is an extendable material having recovery properties. A meltblown web may be extendable, but not have recovery properties and, thus, be an extensible but non-elastic material.

"Elastomeric," "elastic," and "elasticized" refer to a material or composite which can be stretched or elongated by at least 25% of its relaxed length and which will recover, upon release of the applied force, at least 10% of its elongation. It is generally preferred that the elastomeric material or composite be capable of being elongated by at least 100%, more preferably by at least 300%, of its relaxed length and recover at least 50% of its elongation.

"Non-extensible" refers to a material that does not stretch or extend by at least about 25% of its relaxed length without fracture upon application of a biasing force. Materials that are extensible or elastomeric are not considered "non-extensible."

"Untensioned" as used herein to describe a material web does not mean lacking all tension. In order to handle and process moving webs, some moderate amount of tension is needed to hold the web or material in place. An "untensioned" web or material, as used herein, is under enough tension to process the material, but less than that required to cause substantial deformation of the material.

"Necked material" refers to any material, which has been constricted in at least one dimension by processes such as, for example, drawing.

"Neck-bonded" laminate refers to a composite material having an elastic member that is bonded to a member while the member is extended in the machine direction creating a necked material that is elastic in the cross-direction. Examples of neck-bonded laminates are disclosed in U.S. Pat. Nos. 4,965,122; 4,981,747; 5,226,992; and 5,336,545, which are incorporated herein by reference in their entirety for all purposes.

"Reversibly-necked material" refers to a necked material that has been treated while necked to impart memory to the material so that when force is applied to extend the material to it pre-necked dimensions, the necked and treated portions will generally recover to their necked dimensions upon termination of the force. A reversibly-necked material may include more than one layer. For example, multiple layers of spunbonded web, multiple layers of meltblown web, multiple layers of bonded carded web or any other suitable combination of mixtures thereof. The production of reversibly-necked materials is described in U.S. Pat. Nos. 4,965,122 and 4,981,747, incorporated herein by reference for all purposes.

"Stretch-bonded" laminate refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25% of its relaxed length. Such a multilayer composite elastic material may be stretched until the non-extensible layer is fully extended. Examples of stretch-bonded laminates are disclosed, for example, in U.S. Pat. Nos. 4,789,699, 4,781,966, 4,720,415, 4,657,802, and 4,655,760, which are incorporated herein by reference in their entirety for all purposes.

"Neck stretch-bonded" laminate refers a laminate made from the combination of a neck-bonded laminate and a stretch-bonded laminate. Examples of necked stretch bonded laminates are disclosed in U.S. Pat. Nos. 5,114,781 and 5,116,662, which are incorporated herein in their entirety by reference thereto for all purposes. A necked stretch bonded laminate can be stretchable in both the machine and cross-machine directions.

Various aspects and embodiments of the invention will be described in the context of a material for disposable absorbent articles, such as disposable diapers, children's training pants, incontinence articles, feminine care products, diaper pants, disposable swim pants and the like. It should be appreciated that this is for illustrative purposes only, and that the invention is not limited to any particular absorbent article or absorbent articles in general. The material according to the invention may have beneficial uses in any number of applications, such as protective medical clothing, drapes, gowns and the like.

It is to be understood by one of ordinary skill in the art that the present discussion is a description of exemplary embodiments only, and is not intended as limiting the broader aspects of the present invention.

DETAILED DESCRIPTION

Conventional raw material unwinds are designed to maintain consistent tension of non-elastomeric webs at an unwind exit regardless of the diameter of the unwinding roll. By maintaining a consistent tension, a consistent amount of non-elastomeric material is fed into the process in an attempt to achieve a consistent product dimension (e.g., length, circumference, rise, etc.). U.S. Pat. No. 6,314,333 to Rajala et al., which is incorporated herein by reference thereto, describes feeding a consistent amount of elastomeric material into the process.

A through-roll profile unwind control system and method according to the present invention is designed to overcome elastomeric web through-roll variability by automatically adjusting unwind spindle speed based, for instance, on signals from roll-diameter sensors and the use of an unwind equation in accordance with certain aspects of the invention. According to the invention, different material rates are fed into a process based on inherent, predictable through-roll elastomeric stretch properties according to a through-roll referenced stretch-to-stop (rSTS) profile for a consistent maximum product circumference (MPC). More specifically, the "through-roll" or "rSTS" profile and the overall rSTS variability for a given MD elastomeric material are consistent in batch-to-batch, shaft-to-shaft and deckle-to-deckle among elastomeric rolls. Thus, the invention compensates for this predictable through-roll variability, as described in greater detail and by examples below.

Figure 1:
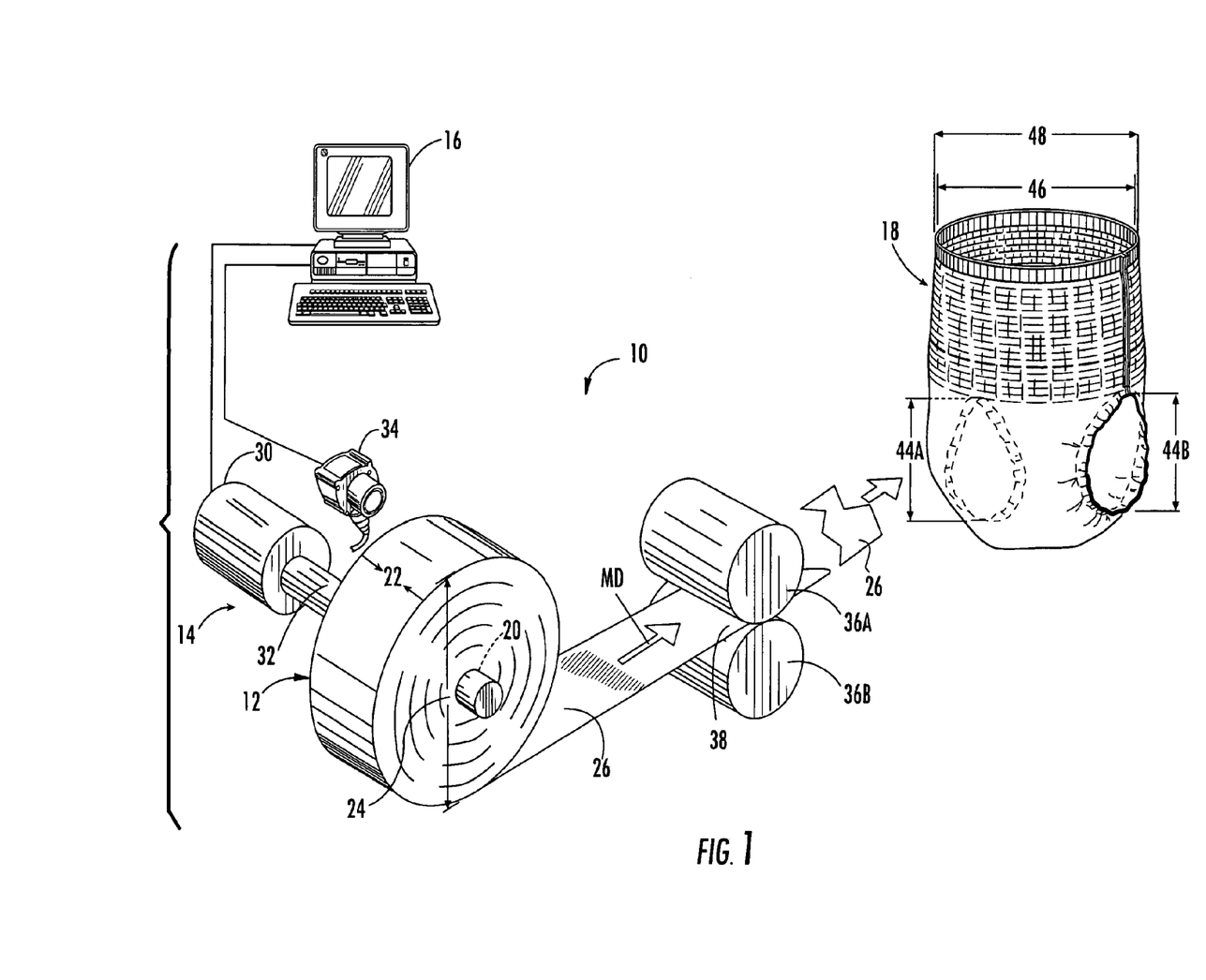
FIG. 1 is a perspective view of one embodiment of a process for producing consistently sized products in accordance with an aspect of the present invention.

With reference now to FIG. 1, a process system is designated in general by the element number 10 and broadly includes a roll of elastomeric material 12, which is unwound by an unwind or unwinder 14 that is controlled by a controller 16 (also referred to herein as a computer or a programmable logic controller (PLC)) to produce a consumer product 18 such as a disposable undergarment. As shown, the roll of elastomeric material 12 has a core 20, which is installed on an unwind shaft or spindle 32 in a manner such as described in U.S. Pat. No. 6,314,333. The unwind spindle 32 is connected to an unwind drive or motor 30, which is controlled by the controller 16 as will be described in greater detail below. The skilled artisan will instantly appreciate that although the controller 16 is depicted as a single desktop computer in this example, the controller 16 can be a PLC, a server, or a variety of computers and combinations of these devices; therefore, the skilled artisan will understand that the process system 10 is not limited to the example shown in FIG. 1.

FIG. 1 also shows a roll diameter sensor 34 connected to the controller 16 for sensing a width 22 and a diameter 24 of the roll of elastomeric material 12. By way of example but not of limitation Sartain et al. teach a system and method of sensing roll diameter in U.S. patent application Ser. No. 10/172,799, which is incorporated herein by reference. Those skilled in the art will appreciate that other roll diameter sensors in addition to the sensor 34 in FIG. 1 can be employed in the process system 10. The roll diameter sensor 34 and additional sensors can be a laser, an electro-optic sensor, an acoustic sensor, an electromagnetic sensor or combinations of these and other sensors for sensing and measuring the roll diameter 24 and depletion of the roll of elastomeric material 12. The skilled artisan will further appreciate that although only one roll of elastomeric material 12 and only one unwind 14 are shown in FIG. 1, additional unwinds and rolls of elastomeric material can be used in the process system 10 to produce the product 18; therefore, the invention is not limited to the example depicted in the figures.

Also shown in FIG. 1, the roll of elastomeric material 12 is unrolled to produce a web of material 26 that is fed in a machine direction (MD) to a plurality of rollers 36A, 36B that form a nip 38. It will be appreciated that the roll of elastomeric material 12 can be a single sheet or a laminate of elastomeric materials. As shown, the web of material 26 is converted into the product 18 using various conversion methods as taught, for instance, by U.S. Pat. No. 6,740,200 to Seymour et al., which is incorporated herein by reference thereto.

As briefly introduced above, one way to understand through-roll variability and to compensate for it is to sample a plurality of rolls similar to the roll 12 described above in order to determine through-roll rSTS variability. An example of through-roll rSTS variability is plotted as a graph 28 in FIG. 2. As shown, the graph or rSTS profile 28 indicates a consistent, average rSTS of MD elastomeric material. The rSTS profile 28 was compiled by unwinding a series of stretch-bonded laminate (SBL) rolls from the top of the rolls to their cores without machine stops. A simulated "print on roll" setup and an ink jet printer were used to print two ink spots per product roll on the unstretched web using an electronic trigger at the start and midpoint of each product. The simulated print on roll setup allowed collection of reference stretch-to-stop data shown as the rSTS profile 28.

Figure 2:
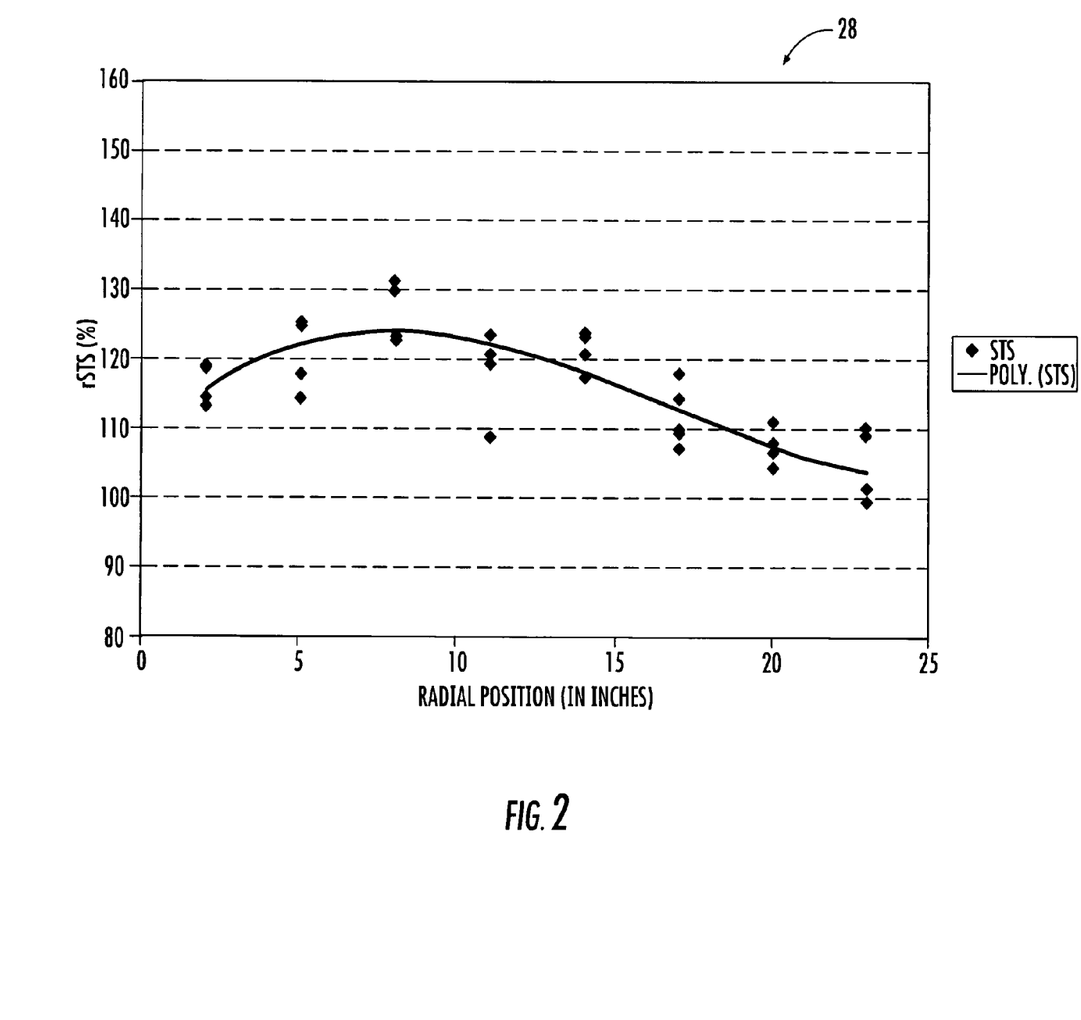
FIG. 2 is a graph of an exemplary referenced stretch-to-stop (rSTS) through-roll profile, which is consistent from batch-to-batch, roll-to-roll and deckle-to-deckle according to another aspect of the invention.

With reference to both FIGS. 2 and 3, using a calculation method according to the invention and knowing a target MPC (discussed below), an unwind feed rate of the web of material 26 can be determined as a function of the roll diameter 24. Shown as a flowchart in FIG. 3, a software program 40 such as an Excel® brand spreadsheet program or a JMP™ brand statistical analysis software program can be used to generate an algorithm or unwind equation 42. The unwind equation 42 is used to compute feed rate in units of length per product in order for the controller 16 to adjust the unwind spindle speed of the unwind spindle 32 to maintain a consistent MPC; i.e., by compensating for the predictable rSTS profile 28. Maintaining consistent MPC ensures that circumferences of leg openings 44A and 44B, a circumference of a waist opening 46, a circumference of a hip 48, or combinations of these circumferences, are consistent from product to product as exemplified by the product 18 in FIG. 1.

Figure 3:
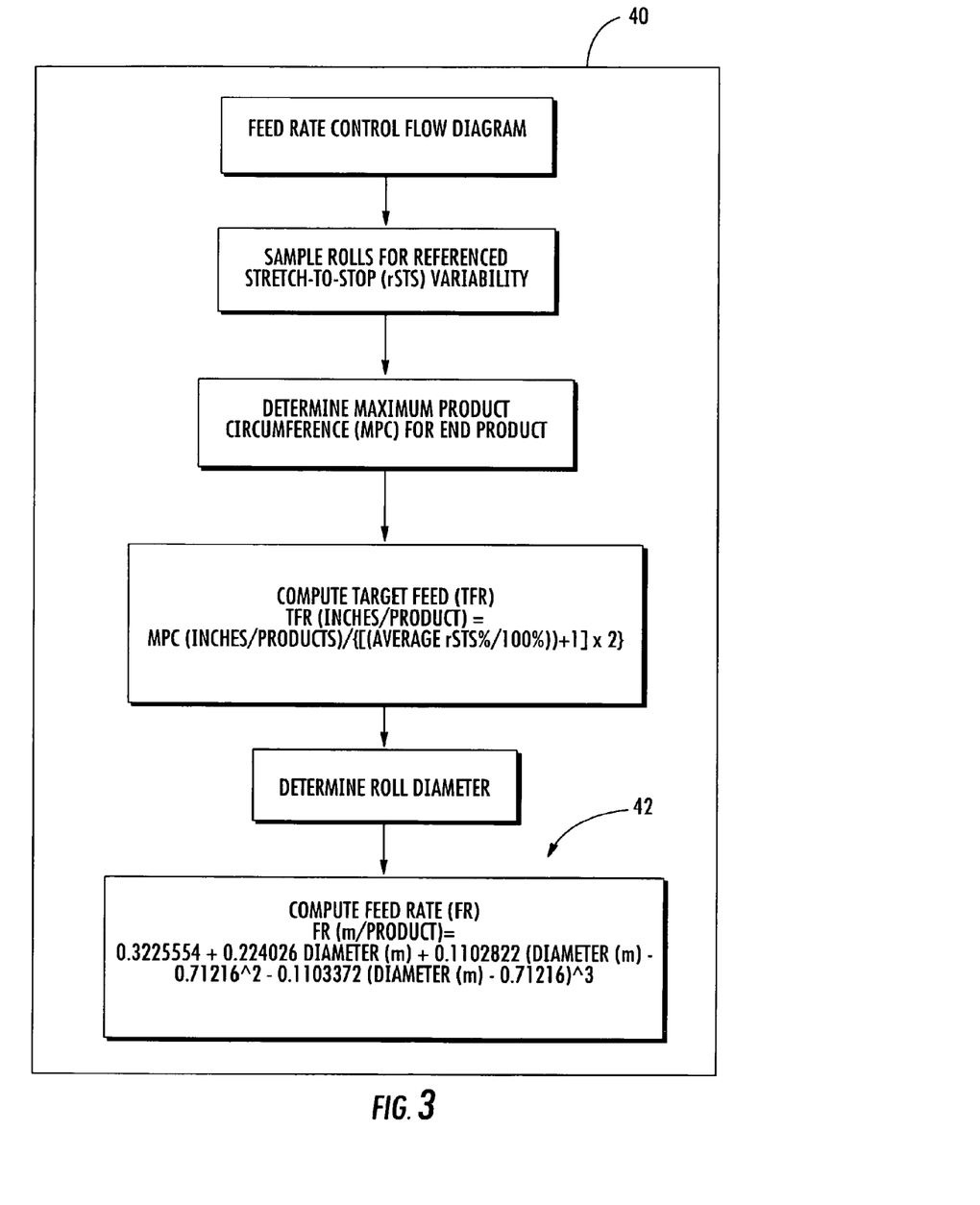
FIG. 3 is a feed rate control flow diagram as a function of the STS through-roll profile in FIG. 2 according to a further aspect of the invention.

With more particular reference to FIG. 3, a feed rate control flow diagram was developed to compensate for the rSTS profile 28. As shown, MPC will normally be defined by consumers by way of product fit studies. Knowing the target MPC and the average rSTS of the MD elastomeric material, the target feed rate of the MD elastomeric material can be determined as follows:

$MPC$ (inches/product)=target feed rate (inches/product)×[(average $rSTS$)(%)÷100%)+1]×2, where front and back panels make up the product circumference of the product 18;

and

Target feed rate (inches/product)=$MPC$ (inches/product)÷([(average $rSTS$ (%)+100%)+1]×2)

For example, if the target MPC is 60 inches/product and the average rSTS for the material is 150%, then target feed rate (inches/product)=60÷([(150%+100%)+1]×2) =60÷5=12. Using the calculation method above and as shown in FIG. 3 and knowing the target MPC for a particular product size, the unwind feed rate can be determined as a function of the roll diameter 24 (see FIG. 1). Accordingly, the equation 42 for the through-roll unwind feed rate data can be generated using various software programs such as the commercially available software programs described above.

Figure 4:
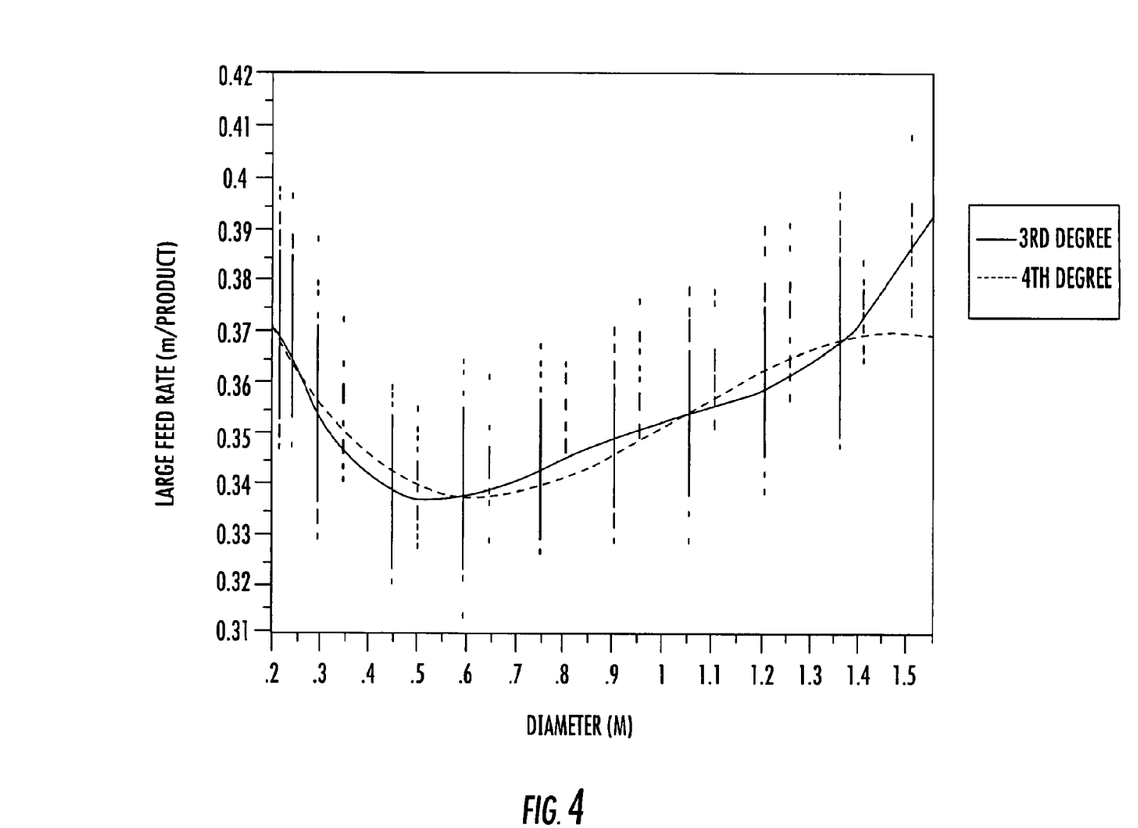
FIG. 4 shows a first through-roll unwind feed rate as a product of the feed rate control flow diagram in FIG. 3 and a second through-roll unwind feed rate based on another high order polynomial feed rate control according to another aspect of the invention.

Turning now to FIG. 4, the most common curve fits for the rolls of elastomeric materials 12 are third and fourth order polynomials as shown in this JMP™ type output for the unwind equation 42. Specifically, a large feed rate for a third order polynomial is graphed in FIG. 4 according to the equation:

large feed rate ($m$/product)=0.3225554+0.0224026 diameter ($m$)+0.1102822 (diameter ($m$)−0.71216) 2−0.1103372 (diameter ($m$)−0.71216) 3.

A fourth order polynomial producing one of the outputs in FIG. 4 is:

large feed rate ($m$/product)=0.3127848+0.0398106 diameter ($m$)+0.0401891 (diameter ($m$)−0.71216) 2−0.2081081 (diameter ($m$)−0.71216) 3+0.2353656 (diameter ($m$)−0.71216) 4.

The skilled artisan will instantly recognize that the feed rate equations above, which produced the results of FIG. 4, can be based on English units (e.g., inches, feet) or Metric units (e.g. centimeters, meters) as depicted above. Additionally, the skilled artisan will recognize that additional higher order equations can be applied to further refine the consistent circumferences required by the product 18.

Figure 5:
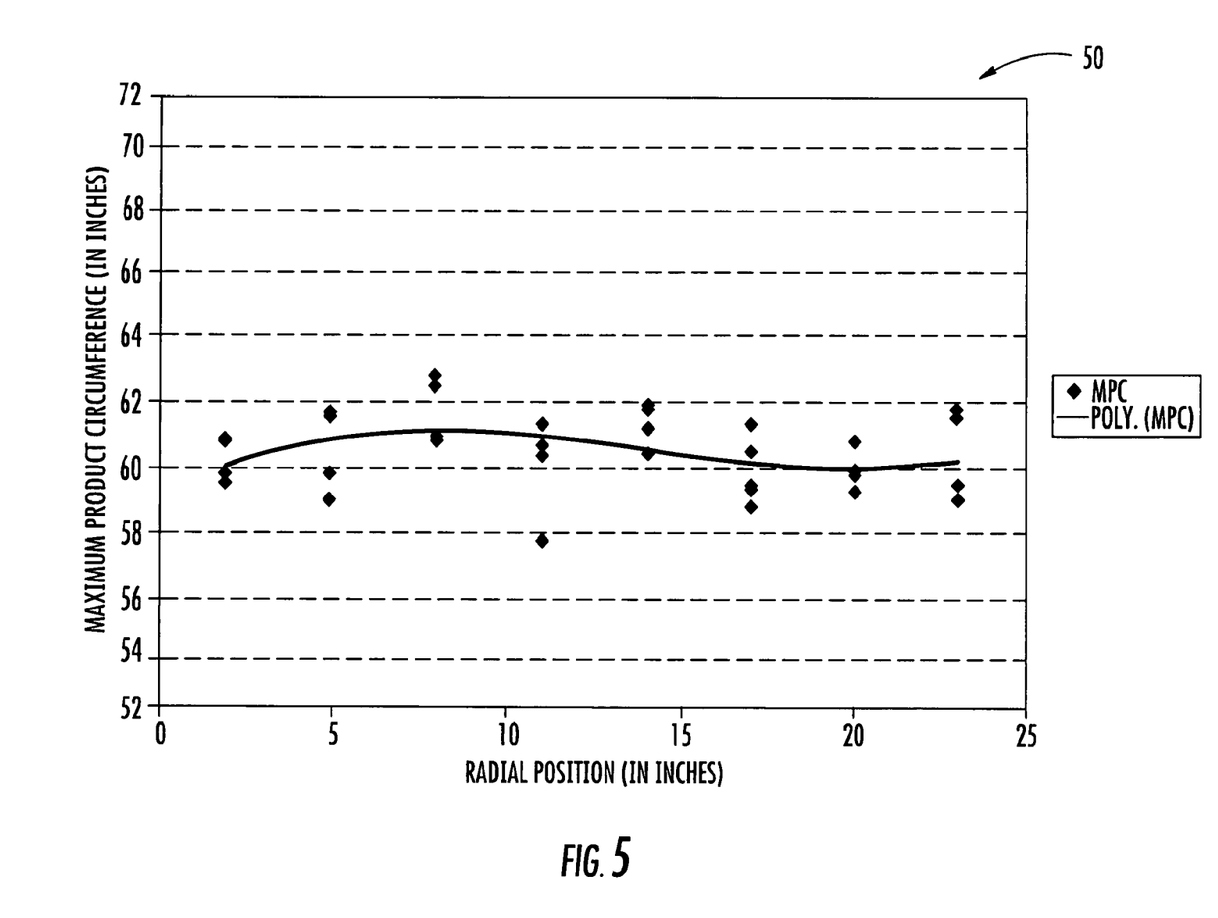
FIG. 5 is a unwind graph showing consistent maximum product circumferences in which the feed rates of FIGS. 3 and 4 compensate for the variable through-roll profile.

FIG. 5 shows a substantially linear output of the web of material 26 based on the foregoing discussion. As shown, a consistent MPC 50 is consistent whether the product 18 is formed from an outer layer of the roll of elastomeric material 12 or from a layer closer to the core 20. More specifically, the unwind equation 42 is used to set the feed rate of the web of material 26 as described above for FIG. 4. Also as introduced above above, the roll diameter sensor 34 is mounted on or near the unwind 14 to calculate the actual role diameter 24. The diameter 24 is fed into the unwind equation 42, which calculates the feed rate in units of length (e.g., inches, meters) per product. The controller 16 then adjusts the unwind spindle 32 to maintain the consistent MPC 50.

Figure 6:
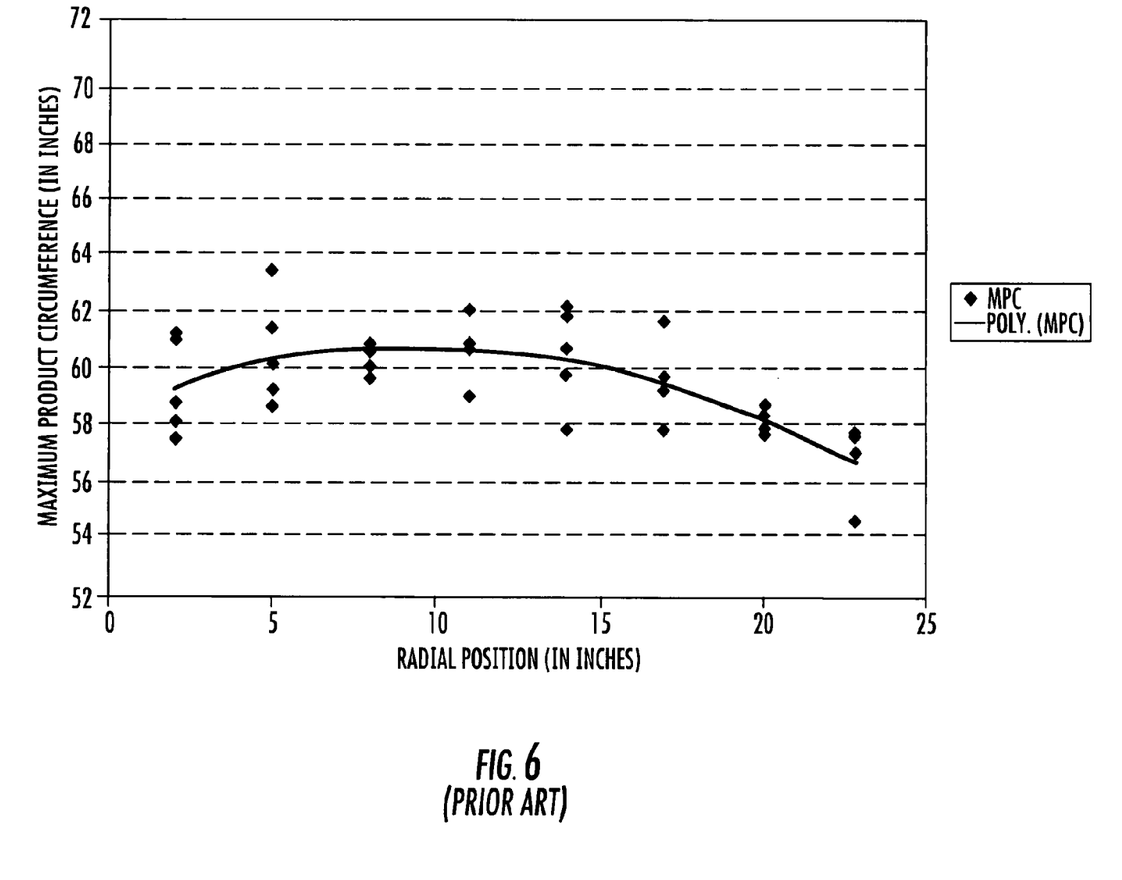
FIG. 6 is an unwind graph showing variable product circumferences defined by through-roll variability when using a conventional constant draw method.

In contrast to the consistent MPC 50 of FIG. 5, maintaining consistent tension as shown in FIG. 6 to input a consistent amount of elastomeric material into a process results in an inconsistent MPC. Thus, the present invention intentionally feeds different material rates on the inherent, predictable through-roll elastomeric stretch properties shown in FIG. 2 in order to get the consistent MPC 50 of FIG. 5.

The invention may be better understood by reference to trials that were conducted to verify that the through-roll profile unwind control method could compensate for the through-roll rSTS variability 28.

EXAMPLE

As noted above, a series of SBL rolls were unwound from the top of the roll to the core without machine stops, and a simulated print-on-roll setup and an ink jet printer were used to print two ink spots per product on the unstretched web using an electronic trigger at the start and midpoint of each product. The simulated print-on-roll setup produced the referenced stretch-to-stop data of FIG. 2.

A Cognex™ brand vision system was used to measure the distance between ink spots at the unwind 14. Material samples were collected while running a constant draw (unwinding the same amount of material per product as is typically done with conventional raw material unwinds) and while using the through-roll profile unwind control method of the present invention. Samples were tested for rSTS using a Syntec™ brand testing machine. Precise Syntec™ jaw spacings were used for testing each diameter position sample. MPC was calculated from the rSTS data and the corresponding jaw spacings using the equation of FIG. 3, however, "two×jaw spacing (inches/product)" was substituted for the target feed rate. MPC results indicated that the through-roll profile unwind control method overcame the through-roll variability as expected (see, e.g., FIG. 5).

Thus, the invention describes an open loop unwind method that passively controls material feed rate of a web of material 26 and MPC by using an equation, such as equation 42 depicted in FIG. 3, derived from elastomeric roll sampling and testing as described above, to control unwind spindle speed of the unwind spindle 32. By using the equation 42 to determine MD elastomeric web feed rate, the method intentionally feeds different material rates based on inherent, predictable through-roll elastomeric stretch properties which is a passive open loop control method unlike conventional closed loop methods that seek to actively control web tension and provide consistent feed rates of consistent amounts of non-elastic material. Accordingly, this method provides improved material consumption levels, less machine waste and consistent product fit and sizing.

These and other modifications and variations to the present invention may be practiced by those of ordinary skill in the art, without departing from the scope and spirit of the present invention, which is more particularly set forth in the appended claims. In addition, it should be understood that aspects of the various embodiments might be interchanged either in whole or in part. Furthermore, those of ordinary skill in the art will appreciate that the foregoing description is by way of example only and is not intended to limit the invention so further described in such appended claims.

That which is claimed is:

1. A method of unwinding material in a process system for producing a product, the method comprising the steps of:
    loading a roll of elastomeric material in an unwind system, the roll of elastomeric material defining a diameter;
    programming a controller with an unwind equation, the controller in communication with the unwind system;
    computing a material feed rate based on a predetermined product circumference and an average stretch-to-stop roll profile;
    inputting the diameter of the roll of elastomeric material and the material feed rate in the unwind equation of the controller; and
    unwinding a varying amount of material from the roll of elastomeric material at a varying unwind speed, the controller being responsive to the unwind equation to vary the unwind speed for forming a plurality of products, each product defining a respective circumference substantially equal to the predetermined product circumference.

2. The method of unwinding as in claim 1, wherein the controller is selected from the group consisting of a computer, a programmable logic controller and combinations thereof.

3. The method of unwinding as in claim 1, wherein the material feed rate is defined as the predetermined product circumference/([(the average roll stretch-to-stop profile/100%)+1]×2).

4. The method of unwinding as in claim 1, wherein the respective circumferences are one of a waist opening circumference, a hip circumference or a leg opening circumference.

5. The method of unwinding as in claim 1, wherein the respective circumference is within a predetermined margin of error of the predetermined product circumference.

6. The method of unwinding as in claim 5, wherein the predetermined margin of error is from about 0.05% to about 5%.

7. The method of unwinding as in claim 1, further comprising the step of sampling a plurality of roll diameters of a plurality of elastomeric rolls to determine the average stretch-to-stop roll profile.

8. The method of unwinding as in claim 1, further comprising the step of sampling a plurality of roll diameters of a plurality of elastomeric rolls from batch to batch, deckle to deckle, or lane to lane within a deckle to determine the average stretch-to-stop roll profile.

9. The method of unwinding as in claim 1, further comprising the step of loading the controller with a statistical analysis program, the statistical analysis program being configured to implement the unwind equation.

10. The method of unwinding as in claim 1, further comprising the step of sensing the diameter of the roll of material with a roll diameter sensor, wherein the sensor is selected from the group consisting of a laser, an electro-optic sensor, an acoustic sensor, an electromagnetic sensor or combinations thereof.

11. A method of unwinding material in a process system for producing a product, the method comprising the steps of:
    determining an average stretch-to-stop roll profile;
    loading a roll of elastomeric material in an unwind system;
    sensing a diameter of the roll of elastomeric material;

programming a controller with an unwind equation, the controller in communication with the unwind system;

computing a material feed rate based on a predetermined product circumference and the average stretch-to-stop roll profile;

inputting the diameter of the roll of elastomeric material and the material feed rate in the unwind equation of the controller; and unwinding a varying amount of elastomeric material from the roll of elastomeric material at a varying unwind speed, the controller being responsive to the unwind equation to vary the unwind speed for forming a plurality of products having substantially similar circumferences.

12. The method of unwinding as in claim 11, wherein the controller is selected from the group consisting of a computer, a programmable logic controller and combinations thereof.

13. The method of unwinding as in claim 11, wherein the material feed rate is defined as the predetermined product circumference/([(the average roll stretch-to-stop profile/100%)+1]×2).

14. The method of unwinding as in claim 11, wherein the circumferences are one of a waist opening circumference, a hip circumference or a leg opening circumference.

15. The method of unwinding as in claim 11, wherein the circumferences are within a predetermined margin of error of the predetermined product circumference.

16. The method of unwinding as in claim 15, wherein the predetermined margin of error is from about 0.05% to about 5%.

17. The method of unwinding as in claim 11, further comprising the step of sampling a plurality of roll diameters of a plurality of rolls to determine the average stretch-to-stop roll profile.

18. The method of unwinding as in claim 11, further comprising the step of programming the controller with a statistical analysis program, the statistical analysis program being configured to implement the unwind equation in the controller.

19. The method of unwinding as in claim 11, further comprising the step of sensing the diameter of the roll of material with a roll diameter sensor, wherein the sensor is selected from the group consisting of a laser, an electro-optic sensor, an acoustic sensor, an electromagnetic sensor or combinations thereof.

20. A process system for unwinding material to produce a product, the process system comprising:

an open-loop unwind system for unwinding a roll of elastomeric material;

a sensor for sensing a diameter of the roll of elastomeric material disposed in the open-loop unwind system; and a controller in communication with the open-loop unwind system and the sensor, the controller being configured for programming with an unwind equation for compensating through-roll variability, the unwind equation being populated with the diameter of the roll of elastomeric material and a material feed rate as a function of a predetermined product circumference and an average stretch-to-stop roll profile, the unwind equation of the controller being configured to vary an unwind speed of the open-loop unwind system such that a varying amount of material from the roll of material is unwound for forming a plurality of products, each product defining a respective circumference substantially equal to the predetermined product circumference.

21. The process system as in claim 20, wherein the controller is one of a computer or a programmable logic controller, and further comprising a statistical analysis program being configured to implement the unwind equation in the controller.

22. The process system as in claim 20, wherein the material feed rate is defined as the predetermined product circumference/([(the average roll stretch-to-stop profile/100%)+1]×2).

23. The process system as in claim 20, wherein the respective circumference is one of a waist opening circumference, a hip circumference or a leg opening circumference.

24. The process system as in claim 20, wherein the respective circumference is within a predetermined margin of error of the predetermined product circumference.

25. The process system as in claim 20, wherein the sensor is selected from the group consisting of a laser, an electro-optic sensor, an acoustic sensor, an electromagnetic sensor or combinations thereof.

* * * * *